United States Patent [19]

Heady et al.

[11] Patent Number: 4,487,832
[45] Date of Patent: Dec. 11, 1984

[54] PROCESS FOR MAKING N-BUTYL BUTYRATE

[75] Inventors: Robert E. Heady, Park Forest, Ill.; Jorge H. Alonso, Montvale, N.J.

[73] Assignee: CPC International Inc., Englewood Cliffs, N.J.

[21] Appl. No.: 442,807

[22] Filed: Nov. 18, 1982

[51] Int. Cl.³ .............................................. C12P 7/62
[52] U.S. Cl. .................................................. 435/135
[58] Field of Search ........................................ 435/135

[56] References Cited

U.S. PATENT DOCUMENTS 1,315,585 9/1919 Weizmann .
2,474,170 6/1949 Sulzbacher .......................... 435/161

FOREIGN PATENT DOCUMENTS 453524 9/1936 United Kingdom .
578279 6/1946 United Kingdom .

OTHER PUBLICATIONS

Matsumura–Chem. Abst., vol. 46 (1952), p. 3211b.
Marvel, et al., *J. Am. Chem. Soc.,* vol. 47 (1925), pp. 3045–3051.
Prescott, et al., *Industrial Microbiology,* 3rd ed., McGraw-Hill Book Company, New York (1959), pp. 250–284.

*Primary Examiner*—Sam Rosen
*Attorney, Agent, or Firm*—Stanley M. Parmerter

[57] ABSTRACT

A novel method for making n-butyl butyrate is disclosed. This method comprises passing a fermentation medium containing solvent-producing cells of *C. acetobutylicum* through a bed of activated carbon followed by desorbing the n-butyl butyrate from the carbon.

10 Claims, No Drawings

PROCESS FOR MAKING N-BUTYL BUTYRATE

FIELD OF THE INVENTION

This invention relates to an enzymatic method for the production of n-butyl butyrate by a fermentation process.

BACKGROUND OF THE INVENTION

The fermentation of carbohydrates to form butyl alcohol and acetone by *Clostridium acetobutylicum* (hereafter abbreviated *C. acetobutylicum*) was disclosed by Weizmann in U.S. Pat. No. 1,315,585. For many years, this process was used for the preparation of acetone and butyl alcohol, and a certain amount of ethyl alcohol was obtained as a by-product.

When the products from the acetone/butyl alcohol fermentation were fractionated, a high-boiling residue amounting to about 0.5 to 1.0% of the total yield of solvents remained in the stills. This was technically known as "yellow oil". Marvel and Broderick, *J. Am. Chem. Soc.*, 47, 3045–3051 (1925), found that the "yellow oil" was a complex mixture of alcohols and esters. Saponification of this mixture and separation of the resulting products gave n-butyl alcohol as the largest alcoholic component of the hydrolyzate and butyric acid as the largest acidic component of the hydrolyzate. These results indicate that a very small amount of n-butyl butyrate is formed in the conventional acetone/butyl alcohol fermentation.

A fermentation process has now been discovered which surprisingly produces much higher yields of n-butyl butyrate. This product is useful as a component of flavors and fragrances and as a solvent.

SUMMARY OF THE INVENTION

In accordance with the present invention, there is provided a process for the production of n-butyl butyrate by a fermentation reaction which comprises first passing a fermentation medium containing solvent-producing cells of *C. acetobutylicum* through a bed of activated carbon whereby n-butyl butyrate is formed and adsorbed on the activated carbon, then desorbing the n-butyl butyrate from the carbon, and finally separating the n-butyl butyrate from other compounds desorbed from the carbon.

DETAILED DESCRIPTION OF THE INVENTION

The process of the present invention is carried out by growing cells of a strain of *C. acetobutylicum* in an aqueous medium which contains one or more carbohydrates that are fermented by this microorganism. The conditions for growing this microbe and its fermentation of carbohydrates to produce acetone/butyl alcohol are well known. These are given in detail in Prescott, S. P. and Dunn, C. G., *Industrial Microbiology*, 3rd ed., pp. 250–284, McGraw-Hill Book Company, New York, 1959, which is incorporated herein by reference in its entirety.

When a good growth of cells of *C. acetobutylicum* has been attained and the cells are actively producing solvents by fermenting the carbohydrates in the medium, the medium containing solvent-producing cells is passed through a bed of activated carbon where production of n-butyl butyrate takes place.

The process of this invention can be carried out in a continuous mode with the growth of *C. acetobutylicum* cells being carried out in a continuous fermentation reactor. The effluent from this continuous reactor is then passed through a bed of adsorptive carbon where the butyl butyrate is formed and adsorbed on the carbon. Other fermentation products are also adsorbed by the carbon, but these can be displaced by the n-butyl butyrate which is preferentially adsorbed as it is formed.

A convenient method for conducting the continuous fermentation which supplies solvent-producing cells to the column is disclosed in a copending patent application, Ser. No. 442,806, titled "Production of Butanol by a Continuous Fermentation Process", filed Nov. 18, 1982, the disclosure of which is incorporated herein by reference in its entirety.

The fermentation process of this invention is carried out using a strain of the microorganism *C. acetobutylicum*. Any strain of this microorganism which produces n-butyl butyrate when fermentation medium containing solvent-producing cells of the microorganism are passed through a bed of activated carbon is suitable for use. A particularly useful strain is the Weizmann strain available from the American Type Culture Collection as ATCC 4259.

The fermentation process of this invention is carried out in a fermentation medium which comprises an aqueous solution containing dissolved carbohydrates, nutrients and growth factors needed for growth of the microorganism. The medium is sterilized before use by heat or other means well known in the art.

The carbohydrates used in the practice of this invention can be any that are fermented by *C. acetobutylicum*. Examples of such carbohydrates are glucose, maltose, sucrose, xylose, and starch or starch hydrolyzates. A low-cost carbohydrate, which is particularly suitable for the process of this invention, is a low dextrose equivalent (D.E.) starch hydrolyzate prepared by the partial hydrolysis of starch with a bacterial alpha-amylase. Nutrients and growth factors required for the growth of the microorganism are added to the fermentation medium. Such nutrients and growth factors are well known to those skilled in the fermentation art. When the fermentation is carried out using the Weizmann strain of *C. acetobutylicum*, only the inexpensive corn steep liquor, readily available from the wet milling of corn is required. This can be supplemented, if desired, with corn gluten.

The pH of the medium is maintained in a range suitable for the growth of the microorganism and for the production of solvents. The fermentation of the present process can be carried out in a pH range of about 4.0 to about 7.0. The pH control of the fermentation can be accomplished by the addition of ammonia using a pH controller that automatically adds the ammonia as necessary to keep the pH in the desired range.

The fermentation is carried out at a temperature range of from about 34° C. to about 41° C. A preferable temperature range is about 35° C. to about 37° C. Temperature of the fermentation is maintained in the desired range by well-known methods such as jacketed fermentation vessels which contain water in the jackets maintained at the desired temperature or by means of heating or cooling coils immersed in the fermentation medium.

The process of the present invention involves passing the fermentation medium, containing cells of the microorganism in the active solvent-producing stage, through a bed of activated carbon. Active fermentation is then continued as the medium and cells are passed through the carbon. It is preferred to pass the mixture upward through the carbon contained in a column since such a process facilitates gas evolution.

Any activated carbon capable of adsorbing butyl alcohol and n-butyl butyrate and which is large enough in granular size to permit the desired flow of the medium through the carbon is satisfactory for use in the process of the invention. An activated carbon made from coconuts available as PCB Pittsburgh activated carbon available from the Calgon Corporation, Pittsburgh, Pa., is suitable for this purpose.

As noted above, the production of n-butyl butyrate by the process of this invention takes place when fermentation medium containing solvent-producing cells are passed through a bed of activated carbon. The rate of flow through the carbon is adjusted so that n-butyl butyrate is produced and adsorbed on the carbon. A flow rate of 0.06 bed volumes per hour (bvh) is suitable for this purpose.

The n-butyl butyrate formed in the process of this invention is removed from the carbon and purified by known processes. A convenient method for eluting the n-butyl butyrate from the carbon involves passing vapors of acetone downward through the column whereby n-butyl butyrate, butyl alcohol and smaller amounts of other compounds formed in the fermentation are removed from the column. This general procedure is described in U.S. patent application Ser. No. 327,849, filed Dec. 7, 1981, the disclosure of which is incorporated herein by reference in its entirety. The n-butyl butyrate is conveniently separated from other materials eluted from the carbon by such means as extraction and distillation.

The procedure of this invention is further illustrated by the following examples, in which all parts and percentages are on a weight basis unless otherwise stated.

EXAMPLE 1

A continuous fermentation was carried out using the C. acetobutylicum strain, ATCC 4259. The fermentation medium was a 10% aqueous solution of Maltrin M-100, a 10 D.E. (dextrose equivalent) corn starch hydrolyzate available from the Grain Processing Corporation, Muscatine, Iowa. The medium also contained 0.75% on a dry substance basis of corn steep liquor. Corn steep liquor is available from the Corn Products Unit of CPC International Inc., Englewood Cliffs, N.J., as code E801. The fermentation was carried out according to the continuous procedure disclosed in a copending patent application, Ser. No. 442,806, titled "Production of Butanol by a Continuous Fermentation Process", filed Nov. 18, 1982, the disclosure of which is incorporated herein by reference in its entirety.

The mixture of medium and cells of the microorganism was pumped from the reactor at the rate of 313 ml/hr. This mixture was passed upward through 2137 g of activated carbon contained in a jacketed, cylindrical stainless steel column, 122 cm long with an internal diameter of 7.29 cm. This gives a flow rate of approximately 0.06 bvh through the column. The carbon used was PCB Pittsburgh activated carbon, 12-30 mesh (U.S. Standard Sieve size with sieve openings of 1.68 mm to 0.59 mm), available from the Calgon Corporation, Pittsburgh, Pa.

The material eluted from the top of the column was discarded. After 55.3 l of effluent had passed through the carbon, the flow was interrupted and the column was allowed to drain by gravity. A drainage mixture of liquid and solid material (980 ml) was collected during 1 hour. Then acetone vapor was passed downward through the column while the temperature of the column was maintained at 54° C. by passing water at this temperature through the jacket surrounding the column. The first fraction eluted (800 ml) was largely water. The second fraction (880 ml) separated into two layers. Subsequent fractions were homogeneous solutions. The composition of the solutions was determined by high resolution, proton nuclear magnetic resonance (NMR) spectroscopy. Results of these analyses are given in Table I. The identification of n-butyl butyrate was made using carbon-13 NMR spectroscopy, comparing the spectrum with that of an authentic sample of the ester. From a total volume of 3.86 l of acetone eluate, there was obtained 351.4 g of butyl alcohol and 161.6 g of n-butyl butyrate. Approximately 31 g of an unidentified lipid material was also eluted from the column.

TABLE I

| Fraction | Volume (ml) | Composition (% by Weight) | | | |
|---|---|---|---|---|---|
| | | Acetone | n-Butyl Alcohol | n-Butyl Butyrate | Water |
| (Drainage) | 980 | 0.3 | 0.8 | — | 97.6 |
| 1 | 800 | 0.4 | 1.0 | — | 96.8 |
| 2 (lower layer) | 510 | 12.6 | 10.4 | — | 71.5 |
| (upper layer) | 370 | 18.7 | 37.7 | 12.1 | 30.9 |
| 3 | 980 | 51.2 | 15.4 | 8.0 | 25.4 |
| 4$^a$ | 980 | 78.4 | 4.9 | 5.6 | 7.9 |
| 5$^a$ | 220 | 80.5 | 3.4 | 6.2 | 6.7 |

$^a$Fractions 4 and 5 contained about 3% of unidentified lipid material.

EXAMPLE 2

The procedure of Example 1 was followed using a fresh sample of PCB Pittsburgh activated carbon in the column. In this experiment, 25 g, dry basis, of gluten slurry obtained from the wet milling of corn was added to the other nutrients in the continuous fermentor each day. When the column was eluted with acetone vapor as in Experiment 1, there was obtained a total of 372 g of butyl alcohol and 131 g of n-butyl butyrate in 3.3 l of eluate. Analysis of the total reaction products indicated that n-butyl butyrate comprises about 12% of the solvents produced.

These examples demonstrate that when a medium containing starch hydrolyzate and corn steep liquor, with or without added gluten, is fermented by C. acetobutylicum in a continuous fermentor and the eluate is passed slowly through adsorptive carbon, a significant quantity of n-butyl butyrate is formed in addition to the butyl alcohol and acetone normally produced by such a fermentation.

COMPARATIVE TEST 1

This test was performed in order to determine the amount of n-butyl butyrate formed in the fermentation reaction which had a very short contact with carbon. A continuous fermentation reaction was carried out as in Example 1 except that the medium contained 1% by weight on a dry substance basis of corn steep liquor rather than 0.75% by weight as in Example 1. The effluent from the fermentor was stored in a container for approximately 100 hours rather than being passed slowly through the carbon column as was done in Example 1. A total of 51 liters of medium was collected which was shown upon analysis to contain 571 g butyl alcohol, 136 g acetone, 200 g butyric acid, 125 g acetic acid and 30 g ethyl alcohol. The concentration of n-butyl butyrate in the fermentation mixture was so small that it could not be measured directly. This ester was concentrated by passing the entire 51 liters of fermentation medium rapidly (10 bvh) through a column containing 405 g of PCB Pittsburgh activated carbon, 12-30 mesh, contained in a column, 58 cm long with an internal diameter of 4.5 cm. Previous experiments have shown that the n-butyl butyrate would be preferentially adsorbed on carbon under these conditions. Elution of the solvents from the carbon column using acetone vapor as in Example 1 gave 5.63 g of n-butyl butyrate and 70 g of butyl alcohol in the eluate. This indicates that approximately 0.76% by weight of the neutral solvents produced in the fermentation is n-butyl butyrate. This experiment clearly indicates that the unexpectedly large percentage of n-butyl butyrate formed in Examples 1 and 2 was formed as the fermentation medium passed slowly through the carbon column.

COMPARATIVE TEST 2

The following test was conducted to determine if esterification takes place on the carbon column in the absence of the microorganism. In a jacketed column of 2.2 cm internal diameter was placed 70 g (180 ml bed volume) of PCB Pittsburgh activated carbon like that used in Examples 1 and 2. The carbon was washed successively with water, 0.1N HCl solution and again with water until the pH of the effluent reached 4.8. The washed carbon was saturated with butyl alcohol by passing a solution of 30 g butyl alcohol in 2 l of water through the column maintained at 40° C. Next a solution of 30 g butyl alcohol and 30 g of butyric acid in 2 l of water was circulated through the column at a rate of 3 bed volumes per hour for a total of 10 hours. The liquid was then allowed to drain from the column and the organic material adsorbed on the column was eluted with acetone vapor using the general procedure described in Example 1. No n-butyl butyrate was detected in the acetone eluate from the column and nearly all of the butyric acid used in the starting solution was accounted for by analysis of the aqueous solutions and the acetone eluate. These results indicate that the formation of n-butyl butyrate does not occur on the carbon column in the absence of the microorganism.

Thus, it is apparent that there has been provided, in accordance with the invention, an improved process for the production of n-butyl butyrate by a fermentation reaction. While the invention has been described in conjunction with specific embodiments thereof, it is evident that many alternatives, modifications, and variations will be apparent to those skilled in the art in light of the foregoing description. Accordingly, it is intended to include all such alternatives, modifications, and variations as set forth within the spirit and scope of the appended claims.

What is claimed is:

1. A process for the production of n-butyl butyrate by a fermentation reaction which comprises first passing a fermentation medium containing solvent-producing cells of *C. acetobutylicum* through a bed of activated carbon whereby n-butyl butyrate is formed and adsorbed on the activated carbon, then desorbing the n-butyl butyrate from the carbon, and finally separating the n-butyl butyrate from other compounds desorbed from the carbon.

2. The process of claim 1 wherein the strain of *C. acetobutylicum* used is ATCC No. 4259.

3. The process of claim 1 wherein the fermentation medium comprises an aqueous solution of a low dextrose equivalent starch hydrolyzate prepared by the partial hydrolysis of starch.

4. The process of claim 3 wherein the fermentation medium further comprises corn steep liquor and corn gluten.

5. The process of claim 1 wherein the fermentation reaction is carried out in a continuous mode.

6. The process of claim 1 wherein the fermentation is carried out at a pH of about 4.0 to about 7.0.

7. The process of claim 1 wherein the fermentation is carried out at a temperature of from about 34° C. to about 41° C.

8. The process of claim 1 wherein the fermentation is carried out at a temperature of from about 35° C. to about 37° C.

9. The process of claim 1 wherein the activated carbon is about 12-30 mesh (U.S. Standard Sieve size with sieve openings of 1.68 mm to 0.59 mm).

10. The process of claim 1 wherein the fermentation medium containing solvent-producing cells are passed through a bed of active carbon at a rate of about 0.06 bvh.

* * * * *